United States Patent

Lankau et al.

[11] Patent Number: 5,817,685
[45] Date of Patent: Oct. 6, 1998

[54] ANTICONVULSIVE IMIDAZOLINE-2,4-DIONES AND PROCESS FOR MAKING

[75] Inventors: Hans-Joachim Lankau; Manfred Menzer; Angelika Rostock; Klaus Unverferth, all of Dresden, Germany

[73] Assignee: Arzneimittelwerk Dresden GmbH, Radebeul, Germany

[21] Appl. No.: 700,876

[22] Filed: Aug. 21, 1996

[51] Int. Cl.⁶ ............... A61K 31/415; C07D 233/74
[52] U.S. Cl. ............... 514/389; 514/391; 548/317.1; 548/320.5; 548/321.1
[58] Field of Search ............... 514/391, 389; 548/317.1, 320.5, 321.1

[56] References Cited

U.S. PATENT DOCUMENTS 5,545,652  8/1996  Itoh et al. ............... 514/383

FOREIGN PATENT DOCUMENTS 5178802  5/1993  Japan .

OTHER PUBLICATIONS

Idi et al, "A Carbon—13NMR Study of, etc" CA 85:191674, 1976.

Waser et al, "Development of New Antiepileptic Drugs, etc" CA 88:69084, 1978.

H.E. Zaugg and D.L. Arendsen–Synthesis of Fused Hydantoins by Intramolecular Amidolkylation pp. 803–806 (1974).

Harvey J. Kupferberg—Strategies for identifying and developing new anticonsulvant drugs. pp. 132–138 (1992).

*Primary Examiner*—Patricia L. Morris
*Attorney, Agent, or Firm*—Schweitzer Cornman Gross & Bondell LLP

[57] ABSTRACT

Anticonvulsive compounds and compositions, of the formula

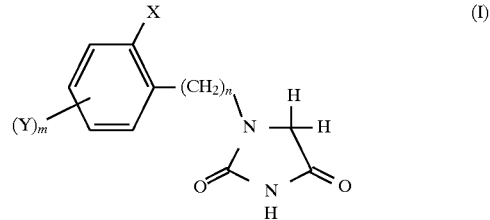

in which X is a $C_{1-4}$-alkyl, trifluoromethyl, or halogen residue, Y is hydrogen or halogen, n is 0 or 1, and m is 0 or a cardinal number from 1 to 4, and its pharmacologically acceptable acid addition salts.

6 Claims, No Drawings

ANTICONVULSIVE IMIDAZOLINE-2,4-DIONES AND PROCESS FOR MAKING

FIELD OF THE INVENTION

The present invention relates to imidazoline-2.4-diones which contain an ortho-substituted ar(alk)yl radical in the 1-position, process for making, and process for treating central nervous system (CNS) disorders therewith, particularly epilepsies of various forms.

BACKGROUND OF THE INVENTION

1-Arylimidazoline-2,4-diones are known which can be prepared by reaction of arylglycines with urea (Ber. 10 2045 (1970); Khim, Geterosikl. Soed. 1978, 87) sodium cyanate (Japanese patent No. 05178802) or potassium cyanate (J. pr. Chem 1926(113), 233) or by cyclization of N-acylurethanes (Drug Res. 1968, 1(1), 189). These known processes do not include the preparation of imidazoline-2,4-diones which contain an ortho-substituted aryl radical in the 1-position which compounds have not been described or otherwise known until now.

A 1-aralkylimidazoline-2,4-dione substituted by a methoxy group on the benzyl radical is described in Japanese Patent No. 05178802. 1-Aralkylimidazoline-2,4-diones can be prepared by reacting appropriate aralkylglycines or aralkylglycine esters with potassium cyanate, and then cyclizing in glacial acetic acid containing hydrogen chloride (J. Het. Chem 11, (1974).

No anticonvulsive action is mentioned or suggested for any of these known compounds. Whereas a number of compounds are known, having anticonvulsive activity, not all epileptic disorders can be satisfactorily treated.

DETAILED DESCRIPTION

It is the object of the present invention to provide novel compounds having favorable antiepileptic activity.

According to the present invention, these novel compounds are 1-ar(alk)ylimidazoline-2,4diones of the formula

[Structure I with X, (CH$_2$)$_n$, (Y)$_m$, N-H, and imidazoline ring]

in which X is a $C_{1-4}$-alkyl, -trifluoromethyl or a halogen residue, Y is hydrogen, or halogen, n is 0 or 1, and m is 0 or a cardinal number from 1 to 4, and its pharmacologically acceptable acid additions salts.

The number of CH$_2$ groups is either 0 such as in the 1-arylimidazoline-2,4-diones, or 1 such as in the 1-aralkylimidazoline-2,4-diones.

The following are examples of specific compounds of formula I:

1-(2,3-dichlorophenyl)imidazoline-2,4-dione;
1-(2,6-dichlorophenyl)imidazoline-2,4-dione;
1-(2-chlorophenyl)imidazoline-2,4-dione;
1-(4-chloro-2-methylphenol)imidazoline-2,4-dione;
1-(2-fluorophenyl)imidazoline-2,4-dione;
1-(2-chlorobenzyl)imidazoline-2,4-dione;
1-(2,6-difluorobenzyl)imidazoline-2,4-dione; and
1-(2,6-dichlorobenzyl)imidazoline-2,4-dione.

According to the present invention, the compounds of the formula I can be prepared by reacting with chlorophenyl isocyanate a compound of the formula:

[Structure II with X, (CH$_2$)$_n$—NH, (Y)$_m$, CH$_2$—COOR]

in which X is a $C_{1-4}$ alkyl, trifluoromethyl, or a halogen residue, Y is hydrogen, or halogen, n is 0 or 1, m is 0 or a cardinal number from 1 to 4, and R is H, or an $C_{1-18}$ alkyl residue.

The reaction is suitably carried out in a solvent at temperatures at from about −20° C. to about 120° C. Suitable solvents include halogenated aliphatic hydrocarbons such as methylene chloride, chloroform and carbon tetrachloride. Aromatic hydrocarbons such as benzene and toluene, as well as aliphatic ethers such as diethylether, tetrahydrofuran and 1,4-dioxane are also suitable as solvents.

1-Aralkylimidazoline-2,4-diones can also be prepared by cyclization through their 5-bromo derivatives with stannic chloride catalysis, to a 6-membered ring, analogously to the process described in J. Het. Chem. 11 (1974) pp. 803–806.

The compounds of the present invention can be used as active ingredients of pharmaceutical compositions. Conventional pharmaceutical excipients and auxiliaries can be used to prepare appropriate pharmaceutical formulations in a manner known per se.

The drugs can be administered parenterally such as intravenously, intra-muscularly, subcutaneously, or orally. The dosage forms can be prepared in a manner known per se, as is customary in pharmaceutical finishing. Suitably dosages can be determined by dosage ranging for anticonvulsive efficacy.

The compounds of the present invention exhibit a strong anticonvulsive activity. They were tested for their anticonvulsive action in vivo after i.p. administration using the international customary mouse animal models described in Pharmac Weekblad, Sc. Ed. 14, (1992) pp.132–138. and shown in Table 1 below.

The most commonly used chemoconvulsant is pentetrazol which can be used as a primary screen for anticonvulsant activity when dosages that produce hindlimb tonic extension are administered. A dose of pentetrazol that produces solely clonic seizures cannot be used as primary screen for new compounds, as phenytoin and carbamazepine have no effect on the blocking of clonic seizures. This test using pentetrazol to induce seizures, used as a primary screen of anticonvulsant activity is referred to in the results below as PEZ.

Seizures can also be induced electrically for the identification of anticonvulsant activity. This test is referred to as the MES test for identifying CNS active drugs. A 50 μA (60 Hz) electrical current for 0.2 s is delivered by a corneal electrode to mice. The current is four to five times as large as the threshold current needed to produce the tonic seizure. These specific parameters are used to identify compounds that prevent seizure spread, therapeutic agents for generalized tonic clonic seizures. Therapeutic agents for absence of seizures are undetected. However, when the current is lowered to 12 μA, compounds which modify both seizure spread and seizure threshold are identified.

After highly active compounds have been identified by a primary screen, more advance mechanistic and seizure type models are needed to refine the choice for an anticonvulsant. Bicuculline produces seizures by competitively antagonizing the action of GABA. Picrotoxin interacts with chloride ionophore of the GABA/benzodiazepine channel complex.

For example, for the compound of Example 8 (1-(2,6-difluorobenzyl)imidazoline-2,4-dione) in the mouse the $ED_{50}$ (i.p.) for the maximum electroshock was determined to be 36 mg/kg, the $ED_{50}$ in the s.c. pentetrazole test was determined to be 50 mg/kg, the $ED_{50}$ in the s.c. pentetrazol test was determined to be 50 mg/kg, and the $NT_{50}$ (i.p.) for the neurotoxicity was determined to be 123 mg/kg.

In comparison to this, known antiepileptics such as carbamazepine and calcium valproate are active either in the maximum electroshock model, or in the pentetrazol test, but not in both.

| Examples | Log p (octanol-$H_2O$) partition coeff. | Test | Dose mg/kg | Action % of Animals |
|---|---|---|---|---|
| 1 | 0.49 | MES[1] | 300 | 100 |
|   |      | PTZ[2] | 300 | 0 |
| 2 | 1.16 | MES | 100 | 100 |
|   |      | PTZ | 100 | 100 |
| 3 | 0.69 | MES | 30 | 100 |
|   |      | PTZ | 100 | 100 |
| 4 | —    | MES | 100 | 100 |
|   |      | PTZ | 100 | 100 |
| 5. | 0.86 | MES | 30 | 100 |
|    |      | PTZ | 30 | 100 |
| 6. | 1.12 | MES | 30 | 100 |
|    |      | PTZ | 30 | 100 |
| 7. | 1.44 | MES | 100 | 100 |
|    |      | PTZ | 100 | 100 |
| 8. | 0.63 | MES | 100 | 100 |
|    |      | PTZ | 100 | 100 |
| 9. | —    | MES | 30 | 100 |
|    |      | PTZ | 30 | 100 |

| Controls | Test | Dose mg/kg | Action % of animals |
|---|---|---|---|
| Carbamazepine | MES | 100 | 100 |
|               | PTZ | 100 | 0 |
| Valproate     | MES | 100 | 0 |
|               | PTZ | 100 | 0 |

[1]MES = maximum electroshock
[2]PTZ = S. C. pentetrazol

The preparation of the novel compounds of the present invention is illustrated with the following examples.

Compounds of Formula I, defined in Examples 1–9 in Table 2 below, are prepared as illustrated next. 0.2 mol of N-arylglycine ester of formula II is dissolved in 250 ml of dichloromethane. 0.25 mol of chlorosulfonyl isocyanate is added dropwise at a temperature of from about −15° C. to about −20° C. After two hours, the precipitated sulfamoyl chloride is separated to obtain the polysubstituted aryl radical, or the methylene chloride is distilled off to dryness to obtain the monosubstituted aryl radical. The solid residue is stirred at 80° C. for one hour with 300 ml of water. After cooling, the precipitate is separated, taken up, and heated under reflux with 200 ml of 20 percent hydrochloric acid for two hours. The clear solution is cooled in an ice bath and the crystal mass obtained is recrystallized from ethanol.

Compounds of formula I of Examples 6–9 in Table 2 below, are suitably prepared as illustrated next. Analogously, as described in J. het. Chem. 11 (1974), 0.2 mol of N-aralkylglycine ester of the formula II is dissolved in 40 ml of 33% hydrochloric acid. 0.25 ml of potassium cyanate, dissolved in 50 ml of water, is slowly added dropwise at room temperature. After 8 hours, the reaction mass is extracted with chloroform, the organic phase is separated and the chloroform is removed by distillation. The oily residue is then heated at 100° C. for two hours with 100 ml of 25% hydrochloric acid. After cooling, the solid product is separated and recrystallized from ethanol.

TABLE 2

| Ex. No. | n | m | X | Y | m. p. °C. | Yield (%) |
|---|---|---|---|---|---|---|
| 1 | 0 | 0 | Cl | H | 186 | 65 |
| 2 | 0 | 1 | Cl | 3-Cl | 155 | 55 |
| 3 | 0 | 1 | Cl | 6-Cl | 182 | 43 |
| 4 | 0 | 0 | F | H | 159 | 66 |
| 5 | 0 | 1 | $CH_3$ | 4-Cl | 202 | 61 |
| 6 | 1 | 0 | Cl | H | 155 | 72 |
| 7 | 1 | 1 | Cl | 6-Cl | 164 | 67 |
| 8 | 1 | 1 | F | 6-F | 138 | 69 |
| 9 | 1 | 0 | $CF_3$ | H | 165 | 66 |

We claim:

1. A compound of the formula

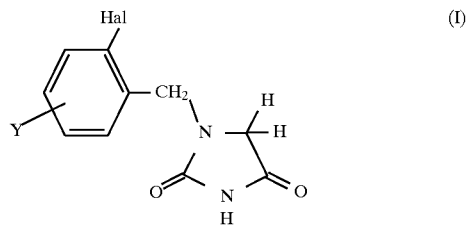

(I)

in which Hal is halogen, Y is hydrogen, or halogen, or the pharmacologically acceptable acid addition salts thereof.

2. The compounds:

1-(2-chlorobenzyl)imidazoline-2,4-dione;
1-(2,6-difluorobenzyl)imidazoline-2,4-dione; and
1-(2,6-dichlorobenzyl)imidazoline-2,4-dione.

3. A pharmaceutical composition comprising as a pharmacologically active substance a compound of claim 1, and a pharmaceutical excipient.

4. A pharmaceutical composition comprising as a pharmacologically active substance a compound of claim 2, and a pharmacological excipient.

5. A process for treating an epileptic disorder in a host, which comprises administering to a host in need therefor an anticonvulsively effective amount of the composition of claim 3.

6. A process for treating an epileptic disorder in a host, which comprises administering to a host in need therefor an anticonvulsively effective amount of the composition of claim 4.

* * * * *